(12) United States Patent
Velez et al.

(10) Patent No.: US 9,635,877 B2
(45) Date of Patent: May 2, 2017

(54) PROCESS FOR OBTAINING HONEY AND/OR FLOUR OF COFFEE FROM THE PULP OR HUSK AND THE MUCILAGE OF THE COFFEE BEAN

(76) Inventors: Andres Ramirez Velez, Medellin (CO); Juan Carlos Jaramillo Lopez, Medellin, CO (US)

( * ) Notice: Subject to any disclaimer, the term of this patent is extended or adjusted under 35 U.S.C. 154(b) by 388 days.

(21) Appl. No.: 14/364,925

(22) PCT Filed: Dec. 14, 2011

(86) PCT No.: PCT/IB2011/055680
§ 371 (c)(1),
(2), (4) Date: Sep. 30, 2014

(87) PCT Pub. No.: WO2013/088203
PCT Pub. Date: Jun. 20, 2013

(65) Prior Publication Data
US 2015/0017270 A1    Jan. 15, 2015

(51) Int. Cl.
| | |
|---|---|
| *A01N 65/00* | (2009.01) |
| *A23L 1/20* | (2006.01) |
| *A23F 5/02* | (2006.01) |
| *A61K 36/74* | (2006.01) |
| *C12P 7/06* | (2006.01) |
| *A61Q 19/00* | (2006.01) |
| *A61K 8/97* | (2017.01) |
| *A23K 10/30* | (2016.01) |
| *A23K 10/37* | (2016.01) |
| *A23L 19/00* | (2016.01) |
| *A23L 33/105* | (2016.01) |

(52) U.S. Cl.
CPC ............. *A23L 1/2005* (2013.01); *A23F 5/02* (2013.01); *A23K 10/30* (2016.05); *A23K 10/37* (2016.05); *A23L 19/07* (2016.08); *A23L 33/105* (2016.08); *A61K 8/97* (2013.01); *A61K 36/74* (2013.01); *A61Q 19/00* (2013.01); *C12P 7/06* (2013.01); *A23V 2002/00* (2013.01); *A61K 2800/10* (2013.01); *Y02E 50/17* (2013.01); *Y02P 60/877* (2015.11)

(58) Field of Classification Search
CPC ...................................................... A61K 36/00
USPC ......................................................... 424/725
See application file for complete search history.

(56) References Cited

U.S. PATENT DOCUMENTS 6,068,866 A * 5/2000 Petrini ................... A23P 20/20
426/138

* cited by examiner

*Primary Examiner* — Michael Meller
(74) *Attorney, Agent, or Firm* — Law Office of Jeff Williams; J. Oliver Williams

(57) ABSTRACT

The present invention relates to a method for using the by-products of coffee in the production of proteins, polyphenols, vitamins and minerals, through methods of concentrating and conserving the mucilage and the pulp (husk) in order to obtain industrially processed coffee honey and/or pulp meal (husk), which is/are suitable for use in products for human or animal consumption, drugs, cosmetics or as raw materials for the production of alcohol for fuel (ethanol), wherein said process makes it possible to reduce the pollution of the environment by avoiding the waste of coffee by-products and to exploit the properties and advantages of same for producing the aforementioned products.

5 Claims, 3 Drawing Sheets

Figure 1:
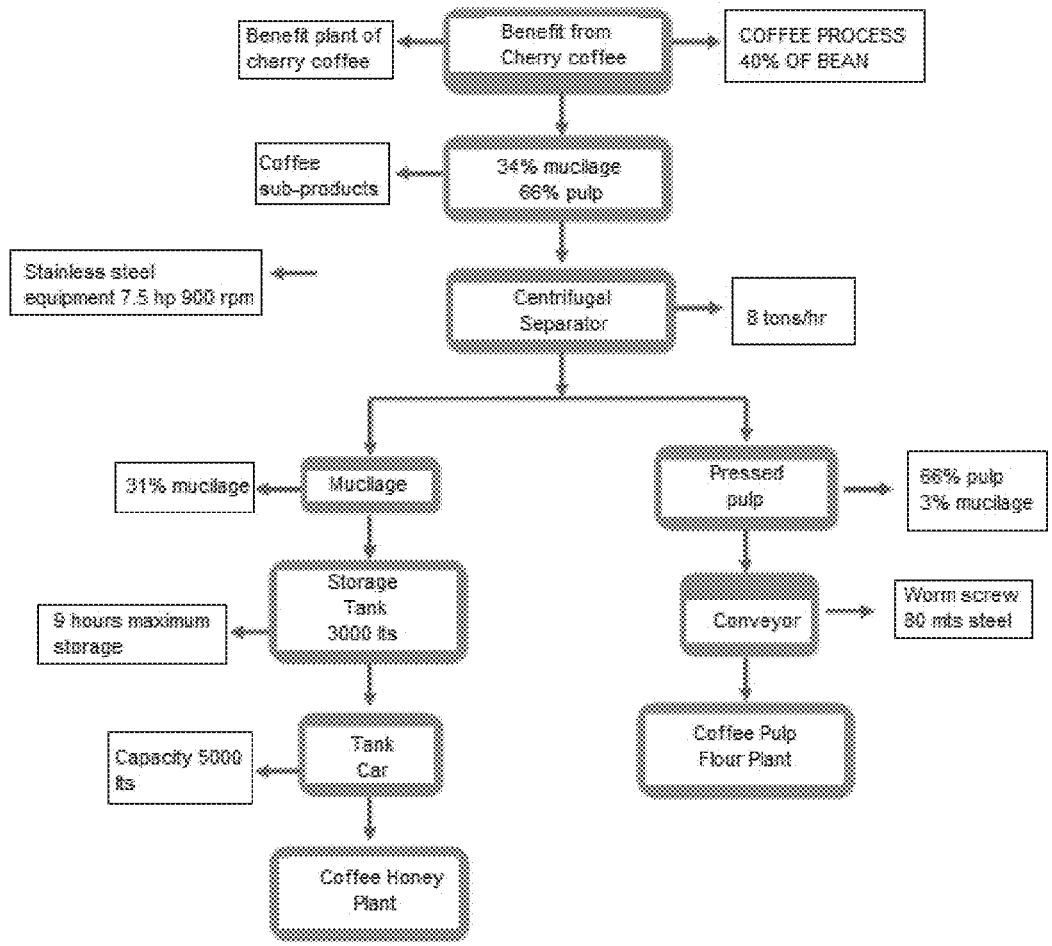

PROCESS FOR OBTAINING HONEY AND/OR FLOUR OF COFFEE FROM THE PULP OR HUSK AND THE MUCILAGE OF THE COFFEE BEAN

CROSS-REFERENCE TO RELATED APPLICATIONS

This application claims priority to PCT Application No. PCT/IB2011/055680, having a filing date of Dec. 14, 2011, the entire content of which are hereby incorporated by reference.

FIELD OF TECHNOLOGY

The following relates to a process for the use of sub-products of coffee in the production of proteins, vitamins and minerals, under processes of concentration and conservation of the mucilage and the pulp (husk) to obtain honey and/or flour of pulp (husk) of coffee industrially transformed in order to be used in products for human consumption, animal consumption, drugs, cosmetics or as raw material for the production of carbonate alcohol (ethanol).

SUMMARY

Likewise, the following is related to the field of the food and/or agro industry, since it refers to the concentration of the mucilage and the pulp (husk) of coffee in an industrial, efficient, safe manner, with high quality standards, with an installed capacity that guarantees the necessary volumes necessary of end product to the customers with high profitability, which also guarantees sustenance in time as well as recovery of the water resources of the influence areas.

BACKGROUND

The handling of sub-products of coffee (mucilage and pulp) has always been considered as one of the problematic axes between producers and coffee specialized centers, notwithstanding at least three options of use have been found: as an element of the compost for fertilizers, as food for pigs, or as raw material for producing ethanol. However, the possibility of using such sub-products of the coffee bean is limited taking into account that the product has a life about 10 hours, whereby it is strictly necessary to process the mucilage and the pulp (husk) before it is decomposed, which implies to make a logistic movement which guarantees the proper use of such sub-products.

Now, the coffee bean is an atypical fruit given that normally fruits are pealed, the pulp is consumed and the seed is disposed or sown. In the case of coffee, the seed is utilized, which is the one being processed and there is a step of drying, roasting and grinding, in order to obtain the coffee which is consumed worldwide, but the sub-products of such coffee bean are eliminated and disposed to the environment, which leads to a high contamination taking into account the degradation time thereof.

Actually, the processing of the coffee bean can be made by means of two methods wherein the first one is made through machinery in dry benefit, wherein the pulping stage is made with no water, wherein although such method is more eco-friendly, it is not very used in most of the countries, namely in the coffee producing ones which are located in the Ecuadorian region. The second method is carried out by the benefit of wetness, that is, using water, to which the quality of the coffee is attributed and corresponds to the most commonly used method in the state of the art. In this process after collecting the coffee, it is located in a receiving tank wherein the first sorting of the coffee by density is carried out, then it is pulped, followed by sorting. Later, the mucilage is removed, which can be carried out by several methods such as the elimination of mucilage by fermentation, sometimes accelerating the process by using an enzyme called pectinase, or using machinery. Next, the coffee bean is washed again with water and is sorted again by density, then the coffee receives a drying process in order to eliminate a large amount of the moisture that has been kept and subsequently it is packed.

In this regard, during the wet benefit of the coffee, sub-products and aqueous effluents are generated which due to the chemical and microbiological composition and by its physicochemical characteristics such as organic load, acidity and content of sediment materials, causing thereby changes on contact with water, and its properties affecting the viscosity of water, color, turbidity, transparency, temperature, odor, surface tensions and flavor, and the oxygen chemical and biological demand increases, causing a biological impact and imbalance in the water ecosystem. Such contamination and substantial reduction of the water consumption has been reduced by means of machines for removing the mucilage (belcosub), which are machines that allow to remove the mucilage in an eco-friendly manner. In this process, a viscous product with high content of solids is obtained, which is also highly contaminated due to its organic load equivalent to about 110,000 ppm (parts per million) of Chemical Oxygen Demand (COD), which also facilitates the conversion at an agricultural, industrial and livestock level and its proper use.

In the same manner, the mucilage of coffee is characterized by having large amounts of carbohydrates, reducing and non-reducing sugars and pectic components. Moreover, it features values of 0.95% protein, 0.08 fat and 0.45% ashes, and in greater proportion elements as K (potassium), Ca (calcium), Mg (magnesium) and P (phosphor) can be found. The caloric value of the mucilage is low, about 500 Kcal/Kg and it is mainly given by the content of carbohydrates.

Now, the protein of the pulp of coffee contains similar or higher amino acid levels than other products, such as cotton flour and soy flour. On the other hand, the pulp of coffee features generally higher concentrations of amino acids than that of corn but is deficient in sulfur amino acids. Also, it is important to note the relatively high content of lysine in the pulp, which is as high as the one in soy flour when expressed as mg/g nitrogen.

According to the above, actually the use of the mucilage and pulp of coffee has been suggested as organic fertilizer in the culture of the red California earthworm, food for pigs, and in the production of biofuels. However, traditionally this sub-products is disposed by pouring it in the creeks or rivers or being accumulated in large amounts, wherein the risk of environmental contamination is increased.

Thus, the residue waters of the coffee pulping and washing process, commonly known as honey water, are considered as one of the great organic contaminations in the coffee industry. The mature grape coffee features a physical composition such that the beans represent 20% of the fruit; accordingly, the pulping process generates 80% of disposal representing a high risk of impact on the environment if not properly treated. The pulping and washing process of 1 kg of coffee generates an amount of water and contaminant material equivalent to that produced by 6 people in one day (Pujol et al. 2001; Hernandez et al., 2000). The concentration of the organic contaminant products in the water being used in the wet benefit of coffee depends on the treatment given before these are re-integrated in a water course. The wet benefits are generally not isolated and in the water courses are contaminants with different origin such as agricultural, livestock activities or human waste.

In this regard, the state of the art contains a plurality of disclosures related to the processing of coffee beans or the fermentation thereof in order to obtain different products. Among such disclosures document KR 20110012653 can be found, which mentions a method for preparing a cosmetic composition containing lactobacilli, fermented coffee extract and being proportioned for improving the antioxidant capacity and to avoid the skin aging and wrinkles. This method for manufacturing a cosmetic composition containing lactobacilli and fermented coffee extract is composed by: a step of spraying the coffee beans and mixing 100 parts per weight of the coffee beans and from 450 to 500 parts per weight of distilled water to obtain a coffee bean solution, a step of agitating the coffee bean solution at 75 to 85° C. for 50 to 70 minutes, a step of cooling the solution from 30 to 35° C. in a closed state, a step of inoculating the solution after the inoculation of the initial volume of 1.3 lactobacilli and fermenting at 30 to 35° C. for 45 to 50 hours to obtain a fermentation liquid of *Lactobacillus*, a step of heating the fermentation liquid at 75 to 85° C. for 8 to 12 minutes, and a step of filtering the fermentation liquid, wherein the starting *lactobacillus* is *Lactobacillus bulgaricus*.

On the other hand, document WO 2006/098733 discloses a method and a kit for testing the fermentation rate, fermentation byproducts and fermentation completion of coffee mucilage, wherein such method consists in testing the fermentation rate of coffee by testing a sample of coffee suspended in water using at least one member of a group of disclosed substrates and test kits and, upon color formation, comparing the resulting color to a color scale to indirectly determine the fermentation rate, fermentation byproducts and fermentation completion. The corresponding kit comprises at least one of a pH testing strip, at least one ethanol testing strip, at least one lactic acid testing strip, and a thermometer.

Now, another disclosure is document MX/a/2008/002559, which relates to a method for treating coffee fruits with or without the pulp, wherein such method comprises the step of contacting the coffee fruits with a solution of a composition selected from the group consisting of active chorine-releasing inorganic and organic compositions, such as calcium oxychloride, dichloroisocyanuric acid and sodium and potassium salts thereof and trichloroisocyanuric acid diluted in a liquid vehicle, for a period of time sufficient to disinfect the coffee skin, pulp and beans, avoid fermentation thereof and neutralize metabolic chemical compositions that are detrimental to flavor, aroma and acidity degree of the coffee and to its quality.

Finally, document EP 1715751 discloses a method for making a coffee composition, which comprises the steps of separating coffee beans from the pulp and husk of a coffee cherry, roasting the coffee beans, and adding dried pulp and/or husk of the coffee cherry to the roasted coffee beans. The invention described in this document also relates to a coffee composition comprising roasted coffee beans and pulp of a coffee cherry and/or husk of a coffee cherry, wherein said in invention relates to a coffee beverage comprising a coffee composition of the invention, and to the use of pulp and/or husk of a coffee cherry to modify the taste of a coffee composition made of coffee beans.

According to the above documents existing in the state of the art related to the process of the coffee bean and its sub-products, the problem to be solved is still the same, the conservation or proper preservation of the product for use in the above mentioned purposes, due to from its collection until its manipulation and stabilization, no more than 10 hours can be elapsed, given that after such time, the mucilage and the pulp being to deteriorated since when a fruit is peeled its natural protection is eliminated initiating thereby a normal process of decomposition, which from a logistic handling point of view becomes a critical point which makes it difficult the effective treatment of such sub-products of coffee and its real use, taking into account that in terms of time of coffee benefit, the bean is the main actor, relegating to the background the treatment of sub-products, becoming thereby in a great storage and disposal problem, which are mostly disposed to the environment, contaminating it as previously indicated.

Similarly, the current research related to coffee, are focused on techniques or improvements to the production process of coffee, its preparation or the quality of the coffee, which can be found in the documents related as art and mentioned above, which mention the mucilage but do not specifically or directly refer to such component but to the production or quality of the coffee in a general manner.

In this regard, there is a need in the state of the art for providing a proper method or process for processing the mucilage and the pulp of the coffee bean for obtaining products which can be used both for animals and humans, such as food, cosmetics, drugs, among others, which allows to avoid the contamination of the environment by preventing the waste of such coffee sub-products.

SUMMARY

One aspect is a process for obtaining coffee honey from mucilage of coffee bean, characterized by comprising the steps of:
- separating the coffee bean from the mucilage and the pulp (husk);
- evacuating the sub-products (pulp and mucilage) by means of a conveying means in a mixture of 34% mucilage and 66% pulp;
- entering the coffee sub-products and the bean in a centrifugal separator;
- separating the solids having a size greater than 2 mm and the liquids with solids having a size less than 2 mm (mucilage);
- storing the mucilage in a container for a storage time less than 9 hours;
- subjecting the mucilage to enzymatic treatment, wherein the product is stored in three tanks subjected to a heating process at a temperature in the range from 50° C. to 80° C. to reduce the microbial load;
- reducing the temperature of the enzymatic treatment to 45° C. with the addition of 100 ppm of pectolytic enzymes;
- vacuum dehydrating the product obtained in the last step to obtain a product with minimum nutritional damage by heat, with high digestibility and palatability; and
- obtaining a mucilage by elimination of natural water at a concentration of 55° Brix, which corresponds to the raw material for the manufacture of a plurality of products.

BRIEF DESCRIPTION

Figure 2:
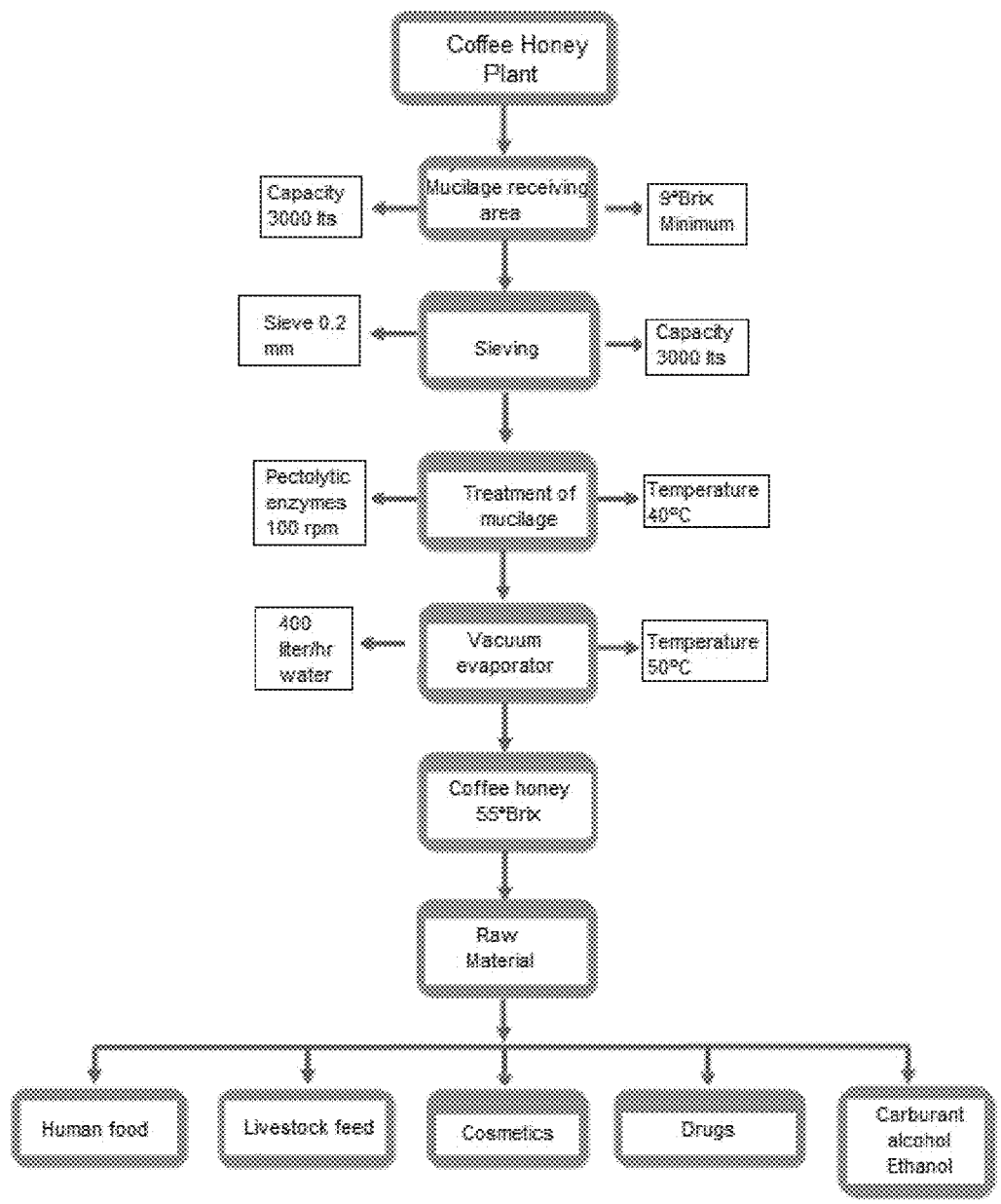
Figure 3:
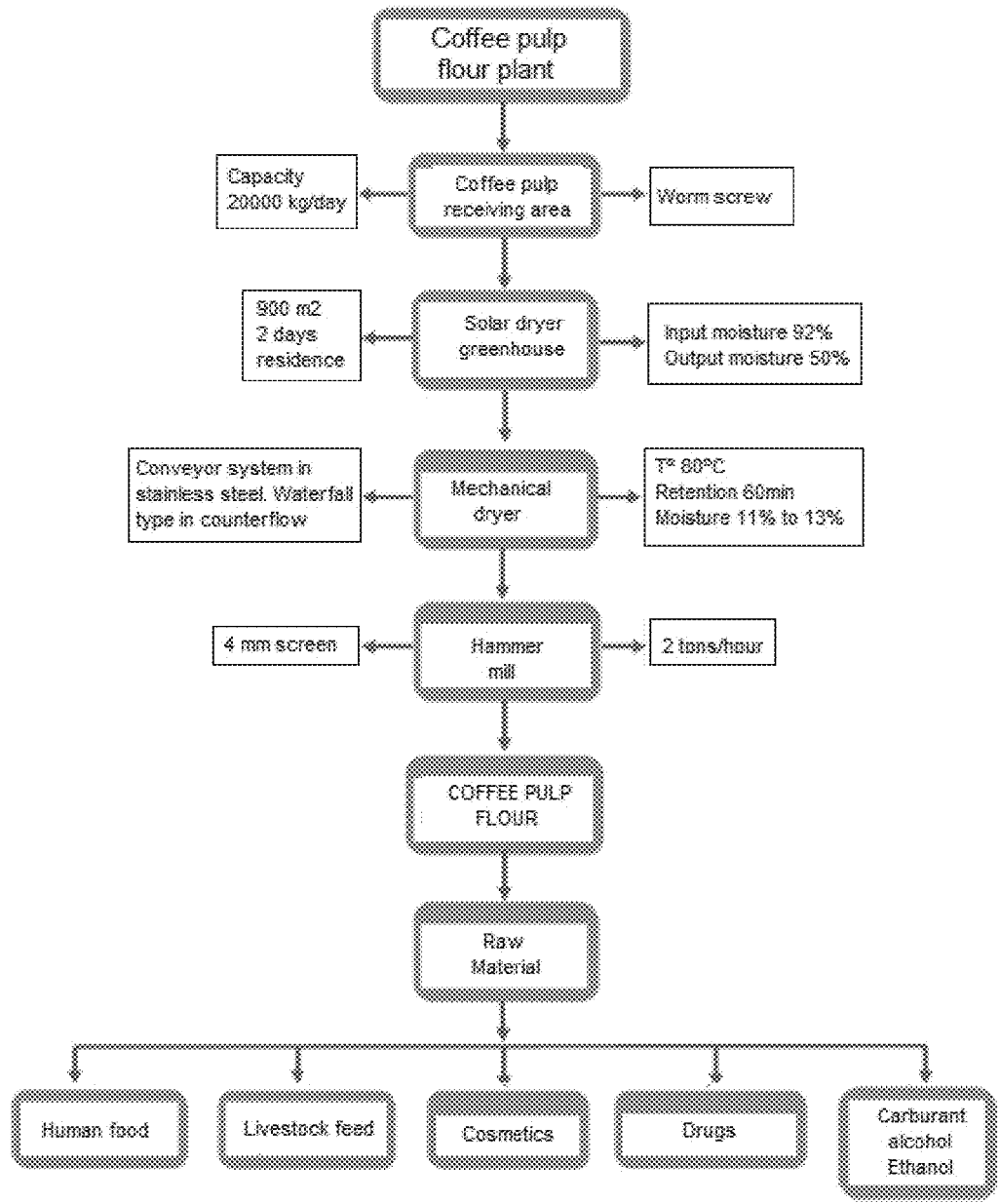

FIG. 1 corresponds to a flow chart for the process of the present invention wherein the separation of the raw materials, i.e. mucilage and pulp of coffee are indicated;

FIG. 2 corresponds to a specific flow chart for the process of obtaining coffee honey from the process of FIG. 1; and FIG. 3 corresponds to a specific flow chart for the process of obtaining coffee flour from the process of FIG. 1.

DETAILED DESCRIPTION

The process of the present invention is based on the use of the coffee bean sub-products which correspond to the pulp or husk and the mucilage, which are used for obtaining coffee honey and coffee flour being used as raw material for the manufacture of a plurality of products due to its high content of antioxidants, proteins and minerals and due to the beneficial properties.

In this regard, when the cherry coffee is harvested, this is sent to the benefit, wherein it is then washed and selected, the coffee bean is peeled from which the seed is obtained in order to continue its dry coffee process and, the sub-products (pulp and mucilage) are evacuated by means of a transportation means, preferably a worm screw, in a mixture of 34% mucilage and 66% pulp, which is fed to a centrifugal separator built in stainless steel with a 2 mm screen, which has a speed of 900 rpm and with a feeding capacity of 8 ton/hour and technologically modified for this kind of product. Then, the equipment proceeds to separate the solids having a size greater than 2 mm (pressed pulp, with 3% mucilage) and liquids with solids having a size less than 2 mm (mucilage). The solids (pulp) are sent to the plant for obtaining coffee pulp flour and the liquids (mucilage) are sent to the plant for obtaining coffee honey, wherein from this point two separate processes are carried out in order to obtain coffee honey from liquid mucilage and coffee flour from solid pulp with 4% mucilage as shown below:

Process for Obtaining Coffee Honey:

The mucilage, which corresponds approximately to 17% of the coffee bean, is stored in a container having a capacity of 5000 liters with a storage time no more than 9 hours, then it is conveyed in a tank car with a capacity of 5000 kg and conveyed to the plant for production of coffee bean after a quality analysis wherein the reading of the Brix degree greater than 9% (sugars) and pH greater than 4.5 (decomposition process) are performed; such readings are carried out with manual electronic equipments easy to handle, wherein such task is made by the operator in charge of collecting mucilage. Below such parameters, the coffee honey is rejected (mucilage represent 10% of the bean but this amount only refers to the mucilage adhered to the bean since the remaining 10% is adhered to the pulp; hence, it is important to feed the separator of the present invention with these two sub-products for its separation and further use).

Initially, the mucilage is passed by a receiving area located in the outer part of the plant for producing honey and comprising an area having a storage tank of 3000 liters, which is connected by a two inch pipe with the next stage.

Then, the mucilage is gravity fed to the centrifugal separator, and its caudal is controlled by a fast action valve which guarantees a flow of about 3000 l/h; the mucilage is passed by a 0.4 mm sieve as raw material for animal food and by a 0.1 mm sieve for human food, and cosmetology in order to eliminate most of the suspended solids, which guarantees a final product completely smooth and free of foreign elements. The separated solids are sent to the flour plant and the mucilage with no solids is send to the enzymatic treating tank. This process is carried out in a sieving area, as shown in FIG. 2.

Now, once the mucilage has passed through the area and the sieving step, it is subjected to an enzymatic treating step, wherein the product is stored in three tanks with a capacity of 10000 liters each subjected to a heating process at a temperature in the range from 50° C. to 80° C., preferably 65° C., in order to reduce the microbial load. After decreasing the temperature at about 45° C., 100 ppm of pectolytic enzymes are added, wherein the pectolytic activity, i.e. the pectinase activity, is to exclusively degrade pectin, wherein such activity is necessary for clarifying the mucilage. This is also important because it anticipates the breaking of walls of the vegetable cells and allows a greater water output in the evaporation process.

Thus, the pectolytic enzymes facilitate the release of the cell content of mucilage and degradation of pectin. The objective of this treatment is to obtain a more stable mucilage, rich in phenolic compounds and also easier to clarify, since the pectin chains prevent the release of the natural water from the mucilage, since when the chains are broken it allows the release of water and increases the concentration of nutrients in the evaporation process and its digestibility. In order to guarantee a proper enzymatic treatment, it is necessary to treat the mucilage at a temperature in the range from 40° C. to 45° C. and with a minimum time of 30 minutes, wherein the greater the enzymatic treatment time, the greater the concentration of sugars and nutrients of the final products and its further use.

Then, the concentrated mucilage or coffee honey (due to its high content of sugars) is achieved by means of a vacuum dehydration step at a temperature no more than 65° C. which allows to obtain a product with a minimum nutritional damage by heat, high digestibility and palatability, which dry material is constituted almost entirely by amino acids and reducing and non-reducing sugars with a life of at least six months in environmental conditions and stored at room temperature from 18° C. to 30° C., which guarantee its organoleptic and microbiologic characteristics.

This treatment begins with mucilage in a concentration of about 7 to 11° Brix, preferably 9° Brix (% sugars) and by elimination of natural water is taken to a concentration of 55° Brix guaranteeing thereby the following final product or raw material characteristics:

TABLE 1

Compositional Analysis

| Composition | % |
|---|---|
| MOISTURE | 30-40 |
| GROSS ENERGY Cal/g | 2345 |
| PROTEINS | 4.46 |
| RAW FIBER | 2.35 |
| FAT | 0.00 |
| ASHES | 2.35 |
| SULFUR | 0.08 |
| CALCIUM | 0.18 |
| COPPER ppm | 10.59 |
| PHOSPHOR | 0.07 |
| IRON ppm | 135.29 |
| MAGNESIUM | 0.04 |
| MANGANESE ppm | 38.82 |
| POTASIUM | 0.69 |
| SODIUM | 0.05 |
| ZINC ppm | 4.71 |
| BRIX DEGREES | 55 |
| POLYPHENOLS mg GAE/100 G | 380.3 |

TABLE 2

Sense Characteristics

| Parameters | Specification |
|---|---|
| Color | Characteristic |
| Smell | Characteristic to the product free of foreign smells and putrefaction |

TABLE 3

Physical Characteristics

| Parameters | Specification |
|---|---|
| Presentation | Gelatinous honey |

TABLE 4

Microbiological Analysis

| Parameters | Result |
|---|---|
| *Clostridium perfringens* | Absent in one gram |
| Enterobacteria | 100-500 |
| Brine | Negative |

Finally, once the raw material based on coffee mucilage is obtained, i.e. coffee honey due to its high content of sugars, this raw material can be used for the manufacture of a plurality of products, such as for human feed, livestock feed, cosmetics, drugs and carburant alcohol (ethanol), among others, wherein such products comprise a high content of antioxidants, proteins and minerals, which improve the performance and health of the consumer, whether it is human or animal.

Process for Obtaining Coffee Flour:

FIG. 3 of the present application shows the necessary steps to be carried out for obtaining a raw material corresponding to coffee flour from the coffee pulp.

In this regard, mainly it is important to take into account that the flour from coffee pulp can replace up to 20% corn in formulations of concentrates for animal feed, and in an attempt to process coffee pulp (husk) there is difficulty due to the ratio of mucilage to pulp (husk), which represents between 34% and 66%, in the drying process of mucilage since when evaporated it forms a sugar crystal and the pulp is encapsulated, which does not allow the internal drying, whereby a pressing process was begun with large amounts of mucilage.

Thus, one of the biggest problems in the process of drying fruit pulps is that the moisture of the raw material is too high (about 92%), and it is necessary to be taken to moisture levels between 10% and 14%, which represents to eliminate a moisture percentage between 75% and 80%. This leads to a very high power generation in order to achieve the evaporation of all this moisture percentage, therefore, the technology used for the process of the present invention is the mixture of solar energy and generated energy, as detailed below.

Initially, there is a coffee pulp receiving area, wherein such previously pressed pulp is conveyed by a worm screw with a length in the range from 40 m to 80 m, preferably 60 m, to the solar dryer.

Once the pulp is located in the solar drying area, the product is received in a greenhouse having an area in the range from 600 to 1500 $m^2$, preferably 900 $m^2$, with a concrete floor and a greenhouse type plastic ceiling with side curtains for handling the airflows. Thus, the product is manually watered in layers of 10 cm which allows to store about 90 $m^3$×0.7 density=63 ton of pulp. This also allows to convert in 2 days 63 tons with a relative humidity of about 90% in 35 tons with a humidity of about 50% turning the product every 3 hours to guarantee the elimination of moisture, fungi and odors with a mixer wagon designed for such purpose.

If this process if made for 13 days, i.e. 26 days per month, a production of approximately 455 tons of pulp is generated with a moisture content of about 50%, which is passed through a turbo dryer which eliminates lumps and particulates the pulp and eliminates the relative humidity thereof, which allows to accelerate the drying processes.

Then, it is moved to the industrial mechanical drying area, wherein the drying is carried out from the solar yard wherein the moisture was reduced to about 50% until reaching saturation (10% to 12% moisture), which is fed by a worm screw type elevator guaranteeing a continuous flow and balancing the steam pressure of the conveyor and the air. This industrial drying is carried out in a tunnel type dryer with stainless steel conveyors, wherein the coffee pulp with a moisture of about 50% is conveyed by the 4 m long conveyors system over eleven conveyors, which allows to generate a waterfall effect, guaranteeing thereby the homogenization in the drying by delivering product between trays via gravity and circulation of hot air in counterflow.

In this regard, the drying process produced in the conveyors system dryer for coffee pulp is by means of evaporation and drag, which means that the air must be heated at a temperature over 90° C. in order to produce evaporation of the water contained in the pulp. In this process, the following stages can be considered:

a) Heating: When entering the pulp with a moisture content of about 50%, which is conveyed by a worm screw system from the solar yard to the conveyor drying silo and relatively cold (40° C.), a first step is initiated in the dryer which corresponds to heating, wherein in such stage the heat requirement is limited since when having a counterflow system, the hot air has already fulfilled the drying vaporization phase, achieving that the pulp can reach a temperature of about 70° C.

The heating is slow causing the evaporation of water, since when evaporated the water increases 500 times its volume whereby the drying is slow and gradual. The incoming heat distribution in the conveyor silo is over the opposite side, and it is the area with less thermal concentration, which is appropriate.

b) Vaporization: To correctly understand what happens in this stage, it is necessary to consider that there is always a production of a migration of moisture from the coffee pulp to the counterflow hot air, reaching about 15% humidity and normal conditions of pressure and temperature. Inside the dryer, a very slow displacement of the moisture (drying) is produced which increases when increasing the temperature of the final product at about 80° C.

Thus, in this stage, when the pulp reaches higher temperatures the water mass transfer is accelerated from the pulp to the circulating gases, the dryer depending on the capacity of the gases to continue receiving moisture being evaporated, with the speed necessary to not have saturation of moisture from the air. Moreover, in this stage most of the amount of heat is consumed, maintaining the thermal conditions and the conveying speed of the pulp, and the thickness of the layer is about 25 mm.

c) Drying: this stage is characterized by the reduction of moisture of the coffee pulp flour up to minimum levels (10% to 12%), producing thereby the displacement of moisture mainly by dragging. This stage results slower, due to the fact that the moisture migrates each time less easily.

d) Stabilization: This final stage basically consists in the output area where the coffee pulp flour remains substantially dry with no exposure to heat, in contact with the atmospheric air, whereby it could also be called as cooling step. Taking into account that the reduction of moisture could achieve values less than the balance point (12%), as it is contacted with air, the balance will stabilize between the steam pressures of the coffee pulp flour and the air, this condition also depending on the relative humidity of the atmospheric air.

Also in this stage, the quality control of the flour output in the dryer is made, allowing to directly check if the drying process has been correctly developed.

Finally, there is a final step in the hammer mill drying area, wherein the product after stabilized is passed through a hammer mill with a screen of approximately 4 mm and a capacity of about 4000 kg/h to be then packed, stored and commercialized.

According to the previously described process, below is a table with compositional analysis.

TABLE 1

Compositional Analysis

| Composition | % |
|---|---|
| MOISTURE | 9-12 |
| GROSS ENERGY Cal/g | 3883 |
| PROTEINS | 10.5 |
| RAW FIBER | 18.1 |
| FAT | 1.64 |
| ASHES | 2.35 |
| SULFUR | 8.2 |
| CALCIUM | 0.4 |
| COPPER ppm | 16 |
| PHOSPHOR | 0.13 |
| IRON ppm | 756 |
| MAGNESIUM | 0.12 |
| MANGANESE ppm | 85 |
| POTASIUM | 3.82 |
| SODIUM | 718 |
| ZINC ppm | 5 |
| BRIX DEGREES | 5.85 |
| POLYPHENOLS mg GAE/100 G | 7486 |

TABLE 2

Sense Characteristics

| Parameters | Specification |
|---|---|
| Color | Characteristic |
| Smell | Characteristic to the product free of foreign smells and putrefaction |

TABLE 3

Physical Characteristics

| Parameters | Specification |
|---|---|
| Presentation | Flour |

TABLE 4

Microbiological Analysis

| Parameters | Result |
|---|---|
| Clostridium perfringens | Absent in one gram |
| Enterobacteria | 100-500 |
| Brine | Negative |

According to the previously described process, below is a compositional comparison table between coffee pulp flour obtained by the process of the present invention and corn.

TABLE 5

Compositional Comparison of Coffee Flour and Corn

| PRODUCT | PROTEIN | FAT | FIBER | ASHES | E.L.N % |
|---|---|---|---|---|---|
| Corn | 10.0 | 5.9 | 1.7 | 2.0 | 3650 |
| Coffee Pulp Flour | 10.5 | 1.64 | 18.1 | 8.2 | 3883 |

Examples

According to the information shown above, the object of the present invention was initially to produce molasses as raw material for animal feed and production of ethanol from such contaminant. However, when beginning the tests with pigs feed, there were some big changes in the individuals such as: elimination of diarrheic problems, saving up to 25% in feed, increase in the milk of pregnant pigs, female pigs usually produced 9.5 live animals and the rate went to 13 live animals; when born the sucking pigs had an average weight of 1,447 grams and with the honey obtained by the process of the present invention as supplement to the pregnant pigs, the average increased to 1600 gr per sucking pig. In lactation, the pigs have an early weaning at 21 days when the animal reaches an average weight of 6 kg, but with the coffee honey obtained by the process of the present invention, the animal reached such weight at 19 days. It should be noted that these industrial results were obtained in a farm with 4000 animals and at a digestive level the pig is the closest one to humans. Therefore, it can be declared that due to the benefits of the coffee honey and the flour obtained with the process of the present invention, it can be guaranteed that it corresponds to a good economical alternative as nutritional and healthy food (nutraceuticals).

The invention claimed is:

1. A process for obtaining coffee honey from the mucilage of coffee cherry, comprising the steps of:
    a) separating the coffee bean from the mucilage and the pulp;
    b) mixing the pulp and the mucilage to form a mixture;
    c) entering the mixture comprising the mucilage and the pulp of step b) into a centrifugal separator containing a screen;
    d) separating the solids of the mixture having a size greater than 2 mm from the liquid phase with solids having a size less than 2 mm in which the mucilage is contained and from which it is recovered;
    e) subjecting the mucilage to a heating process to reduce the microbial load;
    f) subjecting the mucilage to enzymatic treatment; and
    g) vacuum dehydrating the enzymatically treated mucilage from step f) to obtain said coffee honey.

2. The process of claim 1, wherein the mixture comprising the pulp and mucilage contains about 34% of mucilage and about 66% of pulp.

3. The process of claim 1, wherein the centrifugal separator containing the screen is operated at 900 rpm.

4. The process of claim 1, wherein the enzymatic treatment step is carried out in storage tanks having a capacity of 10000 liters each to which 100 ppm of pectolytic enzymes are added.

5. The process of claim 1, wherein the heating process is carried out at a temperature in the range from 50° C. to 80° C.

* * * * *